(12) United States Patent
Mir et al.

(10) Patent No.: US 8,108,023 B2
(45) Date of Patent: Jan. 31, 2012

(54) BLOOD MONITORING SYSTEMS AND METHODS THEREOF

(75) Inventors: Jose Mir, Rochester, NY (US); Dennis Zander, Penfield, NY (US)

(73) Assignee: Infotonics Technology Center, Inc., Canadaigua, NY (US)

( * ) Notice: Subject to any disclaimer, the term of this patent is extended or adjusted under 35 U.S.C. 154(b) by 1497 days.

(21) Appl. No.: 11/279,290

(22) Filed: Apr. 11, 2006

(65) Prior Publication Data

US 2006/0264715 A1 Nov. 23, 2006

Related U.S. Application Data

(60) Provisional application No. 60/670,150, filed on Apr. 11, 2005.

(51) Int. Cl.
*A61B 5/05* (2006.01)
(52) U.S. Cl. .......... 600/347; 600/345; 600/365
(58) Field of Classification Search .......... 600/345–347, 600/365; 435/4, 7.1, 7.4, 14; 422/50, 400–408, 422/410–412, 62, 63, 68.1
See application file for complete search history.

(56) References Cited

U.S. PATENT DOCUMENTS

| | | | |
|---|---|---|---|
| 4,862,894 A | 9/1989 | Fujii | |
| 5,054,896 A | 10/1991 | Margolis | |
| 5,097,810 A | 3/1992 | Fishman et al. | |
| 5,099,857 A | 3/1992 | Baldo et al. | |
| 5,457,041 A | 10/1995 | Ginaven et al. | |
| 5,680,858 A | 10/1997 | Hansen et al. | |
| 5,953,411 A * | 9/1999 | Farrell | 379/406.02 |
| 6,024,925 A | 2/2000 | Little et al. | |
| 6,355,054 B1 | 3/2002 | Neuberger | |
| 6,692,456 B1 | 2/2004 | Eppstein et al. | |
| 6,934,438 B2 | 8/2005 | Hoke | |
| 7,004,928 B2 | 2/2006 | Aceti et al. | |

(Continued)

FOREIGN PATENT DOCUMENTS

EP 1086718 B1 3/2001
(Continued)

OTHER PUBLICATIONS

Cula et al., "Bidirectional Imaging and Modeling of Skin Texture," Proceedings of Texture, Nice, France, 6 pages (Oct. 17, 2003).

(Continued)

*Primary Examiner* — Patricia Mallari
*Assistant Examiner* — Michael D'Angelo
(74) *Attorney, Agent, or Firm* — LeClairRyan, a Professional Corporation (57) ABSTRACT

A blood monitoring system is capable of monitoring the blood of a subject in vivo. The blood monitoring system comprises: 1) an array of movable microneedle micromachined within associated wells; 2) array of motion actuators able to move each needle in and out of their associated wells; 3) array of microvalves associated with each microneedle able to control the flow of air around the microneedle; 4) an array of chemical sensors inserted into patient by movable microneedles; 5) an array of inductors able to measure chemical concentration in the vicinity of inserted chemical sensors; 6) conducting vias that provide timed actuating signal signals from a control system to each motion actuator; 7) conducting vias that transmit signal produced by array of chemical sensors to the control system for processing, although the blood monitoring system can comprise other numbers and types of elements in other configurations.

28 Claims, 8 Drawing Sheets

U.S. PATENT DOCUMENTS

| | | |
|---|---|---|
| 2002/0087056 A1 | 7/2002 | Aceti et al. |
| 2002/0138049 A1 | 9/2002 | Allen et al. |
| 2003/0083680 A1* | 5/2003 | Jousson .................. 606/161 |
| 2003/0083686 A1 | 5/2003 | Freeman et al. |
| 2003/0153900 A1* | 8/2003 | Aceti et al. ............. 604/890.1 |
| 2003/0208113 A1 | 11/2003 | Mault et al. |
| 2003/0218756 A1 | 11/2003 | Chen et al. |
| 2004/0138541 A1* | 7/2004 | Ward et al. ................ 600/345 |
| 2004/0176701 A1 | 9/2004 | Fujii |
| 2005/0171480 A1 | 8/2005 | Mukerjee et al. |
| 2005/0228313 A1 | 10/2005 | Kaler et al. |
| 2005/0228340 A1 | 10/2005 | Cleary et al. |
| 2006/0002636 A1 | 1/2006 | Torre-Bueno et al. |
| 2006/0049209 A1 | 3/2006 | Baker |
| 2007/0276211 A1 | 11/2007 | Mir et al. |

FOREIGN PATENT DOCUMENTS

| | | |
|---|---|---|
| WO | 01/80728 A1 | 11/2001 |
| WO | 03/092487 A1 | 11/2003 |

OTHER PUBLICATIONS

Office Action from the United States Patent and Trademark Office for U.S. Appl. No. 11/995,366 (Apr. 29, 2010).

Schuster et al., "Macro-Video Documentation Patch Tests," Contact Dermatitis 52:177-83 (2005).

DFW-V500, Technical Manual (Ver. 1.0).

Litwiller, Dave, "CCD vs. CMOS: Facts and Fiction", Jan. 2001 Photonics Spectra.

Prinz, et al., "Automatic Measurement of Skin Wheals Provoked by Skin Prick Tests", Connecting Medical Informatics and Bio-Informatics, IOS Press, 2005; EFMI, pp. 441-446.

Proximity Series. InfiniMini.

Ian Hunter, Minimally Glucose Sensor and Insulin Delivery System, pp. 1-17; Phase 2 Final Report: Sep. 30, 2000; MIT Home Automation and Healtcare Consortium.

K.G. Ong, Magnetism-Based Remote Query Glucose Sensors; Sensors 2001, 1, 138-147; http://www.mdpi.net/sensors.

Chong H. Ahn, Micromachined Planar Inductors on Silicon Wafter for MEMS Applications; pp. 866-876; IEEE Transactions on Industrial Electronics, vol. 45, No. 6, Dec. 1998.

Nicolae Damean, Composite ferromagnetic photoresis for the fabrication of microelecteromechanical systems, pp. 29-34; Insitute of Physics Publishing; 2005 IOP Publishing Ltd.

C.A. Grimes, Magnetoelastic sensors for remote query environmental monitoring; pp. 639-646; Smart Mater. Struct. 8 (1999); UK.

* cited by examiner

BLOOD MONITORING SYSTEMS AND METHODS THEREOF

CROSS REFERENCE TO RELATED APPLICATIONS

This application claims the benefit of U.S. Provisional Application No. 60/670,150 filed Apr. 11, 2005, the entire disclosure of which is incorporated herein by reference.

GOVERNMENT SPONSORSHIP

This invention was made with government support under Grant NAG3-2744 awarded by NASA. The Government has certain rights in the invention.

FIELD OF THE INVENTION

This invention relates to blood monitoring systems and methods thereof.

BACKGROUND

Microneedle technology provides a useful minimally-invasive method to sample blood. Due to their small size, microneedles can pierce skin and take minute quantities of blood with minimal impact and or pain to the subject. In spite of their advantages, microneedle systems are still somewhat invasive since they involve the extraction of blood from the patient.

Implanted in vivo sensors provide another means to sample blood chemistry that does not require blood extraction. Unfortunately, in vivo sensors interact with the physiology and are susceptible to degradation during use. It would be desirable to achieve a less invasive approach that would not extract blood from the patient and provide longer measurement times than in prior art in vivo devices.

SUMMARY

This invention provides a highly useful device configuration and convenient fabrication process for dense arrays of microneedles. Unlike the prior art, the invention describes actuators and sensors associated with each microneedle that can sample blood chemistry without extraction. The sensing process is achieved while the needle is inside the patient, minimizing invasiveness and contamination. Due to their high multiplicity, needles are actuated in sequence over extended periods of time, each sensing element being required to make measurements only over a short time period. Due to their dense spacing, many measurements may be made using a single compact array device worn by the subject as a small patch or chip.

DETAILED DESCRIPTION

A blood monitoring system in accordance with embodiments of the present invention comprises an integrated circuit or chip containing a high density array of microneedles in a patch which is attached to patient and makes multiple blood monitoring measurements. The blood monitoring system comprises: 1) an array of movable microneedle micromachined within associated wells; 2) array of motion actuators able to move each needle in and out of their associated wells; 3) array of microvalves associated with each microneedle able to control the flow of air around the microneedle; 4) an array of chemical sensors inserted into patient by movable microneedles; 5) an array of inductors able to measure chemical concentration in the vicinity of inserted chemical sensors; 6) conducting vias that provide timed actuating signal signals from a control system to each motion actuator; 7) conducting vias that transmit signal produced by array of chemical sensors to the control system for processing, although the blood monitoring system can comprise other numbers and types of elements in other configurations.

Figure 1A:
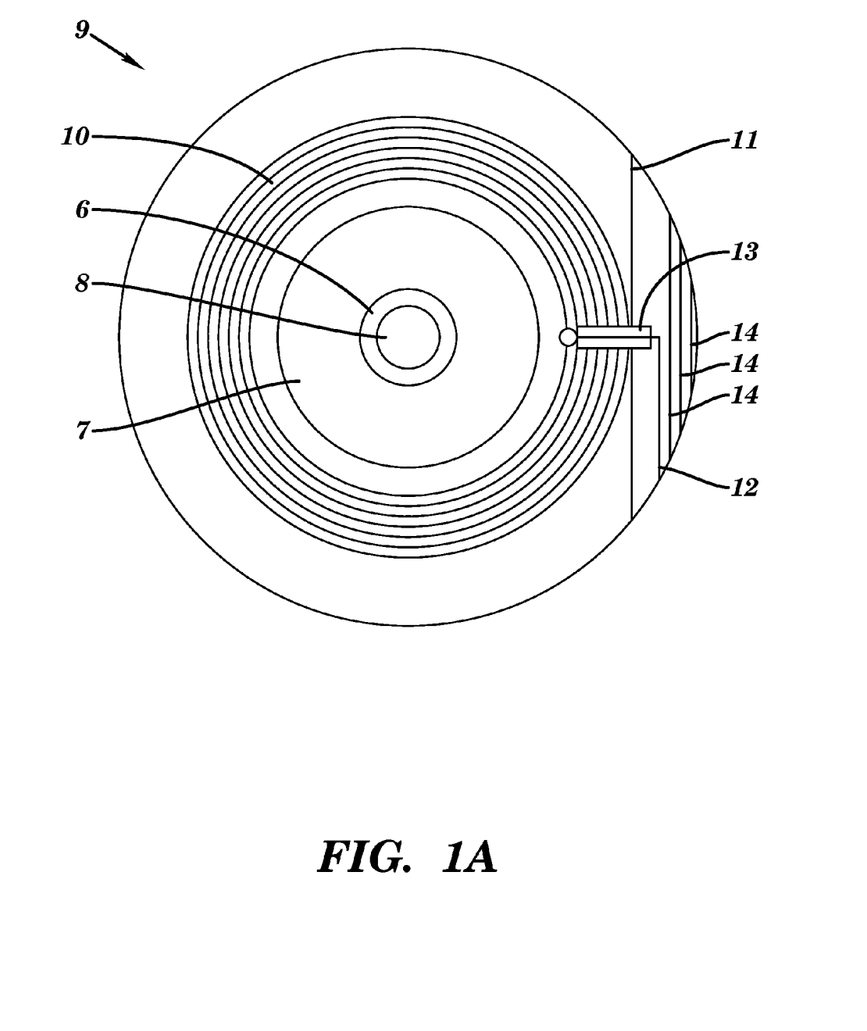
FIG. 1A is a top cross-sectional view of a microneedle assembly in accordance with embodiments of the present invention.
Figure 1B:
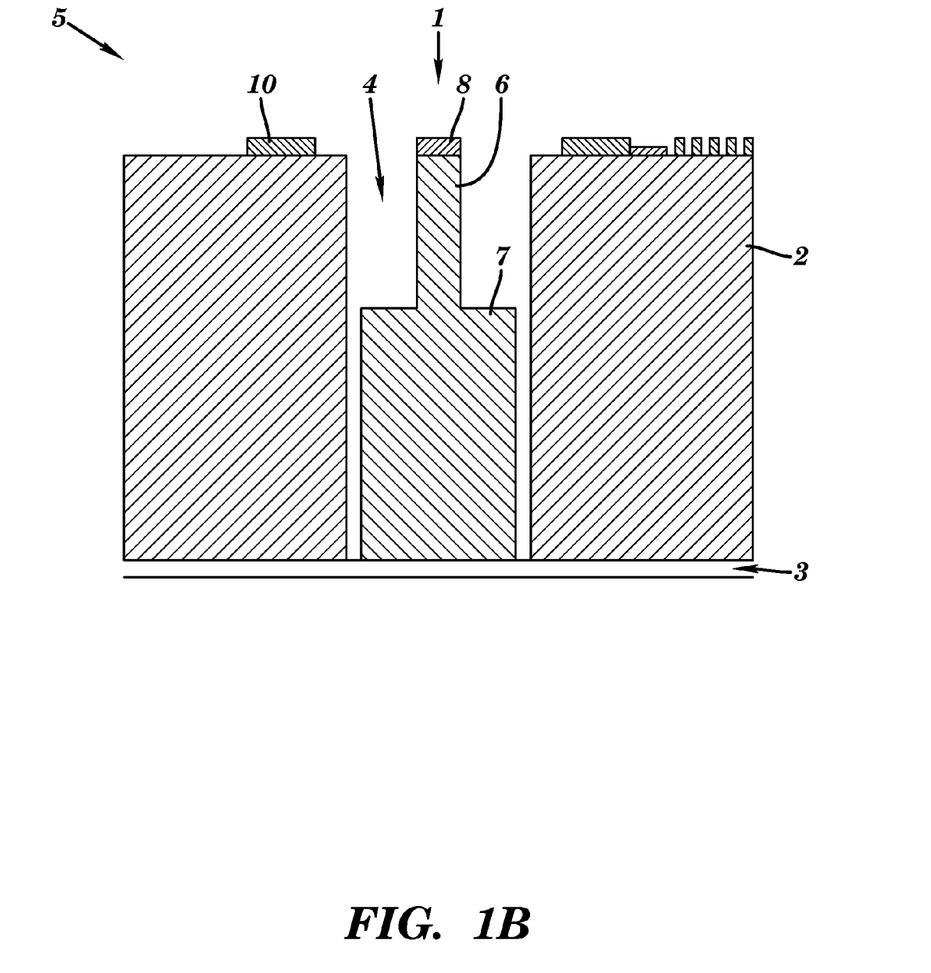
FIG. 1B is a side, cross-sectional view of the microneedle assembly shown in FIG. 1A.

FIGS. 1A and 1B show top and side, cross sectional views of a microneedle configuration. These views depicts microneedle 1 within silicon wafer 2. The microneedle geometry shown may be achieved using photolithography and other well known methods in micro fabrication such as Deep Reactive Ion Etching (DRIE), although other manufacturing techniques can be used. Microneedle 1 is embedded within well structure 4, but remains mechanically attached to silicon wafer 2 through etch stop layer 3 made of materials, such as silicon dioxide or silicon nitride, although other materials can be used.

The microneedle comprises three elements: an upper narrow post 6, a broader lower base 7, and sensing element 8. A magnified top view of the microneedle assembly is shown in FIG. 1A. Sensing winding 10 is patterned in a coil or spiral geometry on the surface of silicon wafer 2. Sensing winding 10 is addressed by common via 11 and signal via 12. Insulator 13 allows signal via 12 to pass over common via 11 and sensing winding 10 without electrical shorting. Common via 11 and other signal vias 14 are used to address other microneedle assemblies.

A control system comprising a processor with programmed instructions stored in memory for execution by the processor of one or more aspects of the present invention as described herein is coupled to the common via 11 and signal vias 14, although other types of systems could be used. The control system is used to control the activation of the microneedles and the readings of the sensing windings. The control system may also process the readings of the sensing windings to provide an output, such as by way of example only a blood sugar level reading or another diagnostic result based on the readings.

Figure 2:
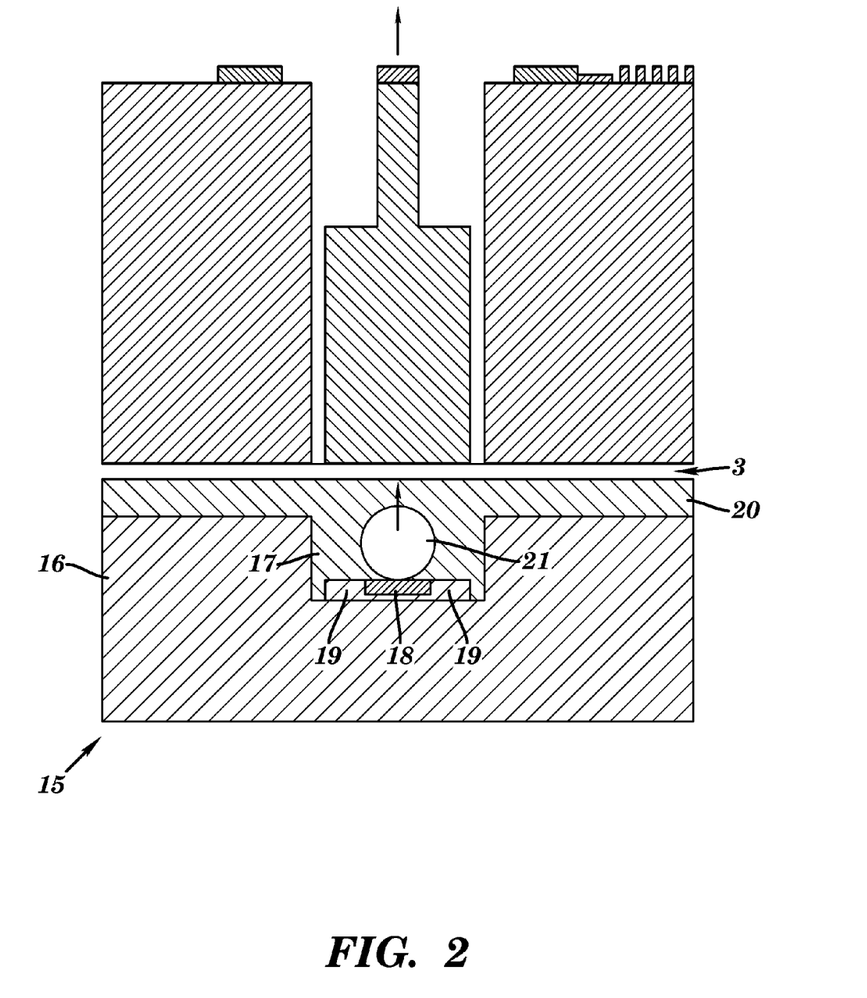
FIG. 2 is a side, cross-sectional view of a microneedle assembly with an integral actuator assembly in accordance with other embodiments of the present invention.

FIG. 2 shows a cross section of a microneedle with an integral actuator assembly 15. Substrate 16 is grooved to create hollow region 17. Liquid channel 20 fills the grooved hollow region 17 with a low viscosity liquid such as water. Resistive element 18 resides within the hollow region 17 along with interconnection electrodes 19. Interconnection electrodes 19 deliver an actuating signal to resistive element 18 causing it to conduct current and to generate heat. The heated liquid in the vicinity of creates a vapor bubble 21 which increases the pressure within region 17 as the bubble expands in volume. The increased pressure in region 17 ruptures etch stop layer 3 and drives the microneedle 1 out of its well structure.

Figure 3A:
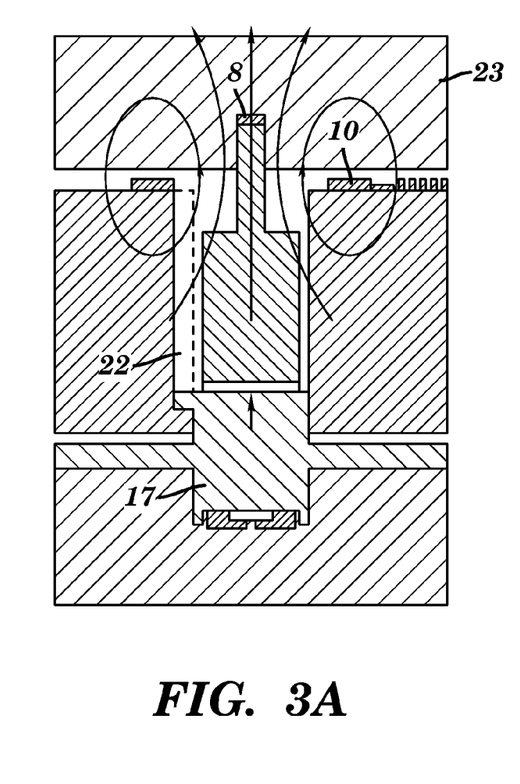
FIG. 3A is a side, cross-sectional view of a microneedle assembly in accordance with other embodiments of the present invention.
Figure 3B:
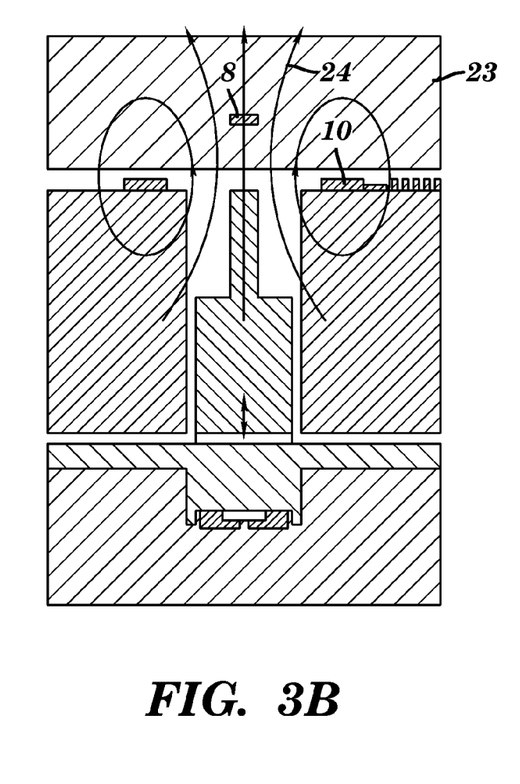
FIG. 3B is a side, cross sectional view of a microneedle assembly in accordance with yet other embodiments of the present invention.

FIGS. 3A-3B, show the actuation process for two microneedle configurations. The microneedle shown in FIG. 3A includes an additional vent slot 22 less than the silicon wafer thickness in depth. As the vapor bubble expands, it drives microneedle 1 into subject 23, stopping its travel after the bottom of base 7 crosses the lower level of vent slot 22. This distance must be sufficient to allow the microneedle enough travel into subject 23, where the measurement needs to be made. For example, in order to measure blood glucose, the needle must penetrate the stratum commune into the dermis or epidermis where interstitial fluid or blood is available. This distance varies according to body location and individual, but is in the range of 30-200 microns.

Following the heating cycle, the vapor bubble collapses, thereby decreasing the pressure in region 17. Vent slot 22 is able to allow air to refill the void created by the collapsing bubble, thus allowing the microneedle to remain inserted in subject 23. As a result, sensing element 8 remains in contact with subject 23, enabling it to sense the desired chemical.

FIG. 3B shows an alternative configuration where the microneedle inserts sensing element 8 into subject 23. Since the configuration of FIG. 3B does not have a vent slot 22, when the bubble collapses during cooling, it pulls the microneedle back toward the silicon wafer. In this case, sensing element 8 is detachable and remains within subject 23 and, therefore, should be biologically compatible. Given its small dimension/volume, the sensor eventually will probably be absorbed in the body.

Figure 3C:
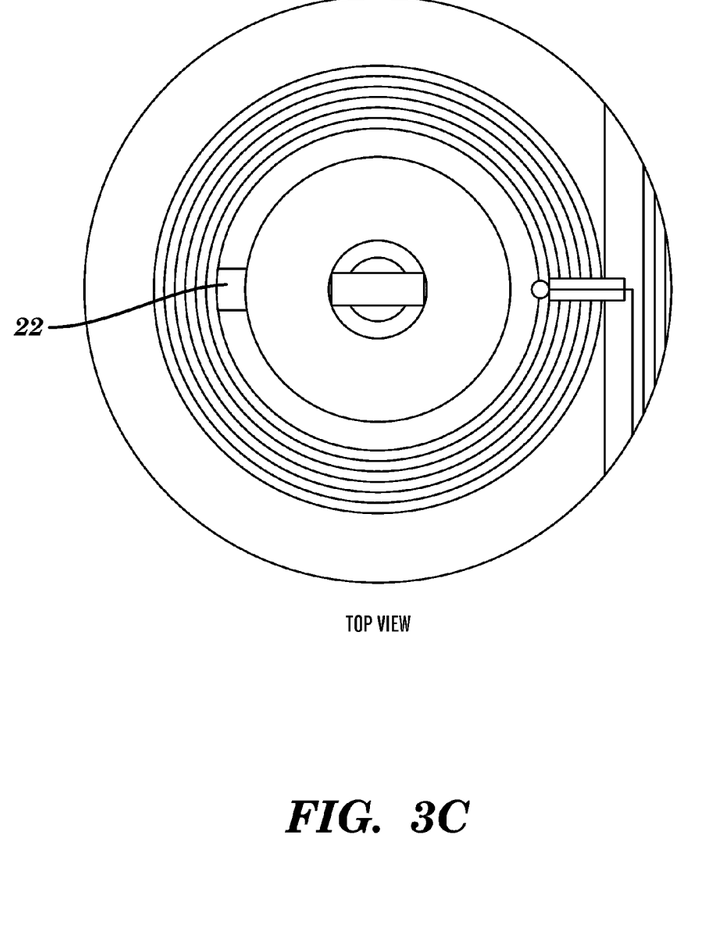
FIG. 3C is a top, cross sectional view of the microneedle assembly shown in FIG. 3A.

FIG. 3A-3C, show how the chemical measurement is made. Current is driven through sensing windings 10, creating a magnetic field depicted by field lines 24. Sensing elements 8 have combined magnetic, inductive, or magnetoelastic properties that vary depending on the chemical composition of the surrounding region of 23. For example, sensing elements 8 may comprise a glucose responsive material (e.g. a polymer) that changes physical properties depending on the local glucose concentration. Sensing elements responsive to other chemicals of interest (e.g. cholesterol) may also be used.

Figure 4A:
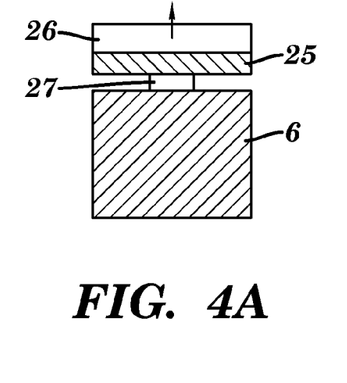
FIG. 4A is a side, cross-sectional view a portion of a microneedle assembly.
Figure 4B:
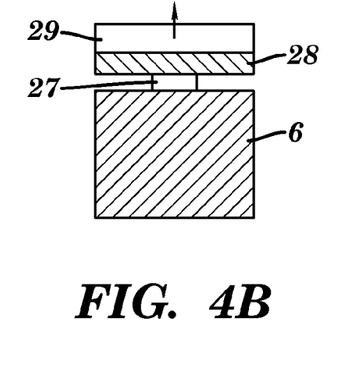
FIG. 4B is a side, cross-sectional view of portion of another microneedle assembly.
Figure 4C:
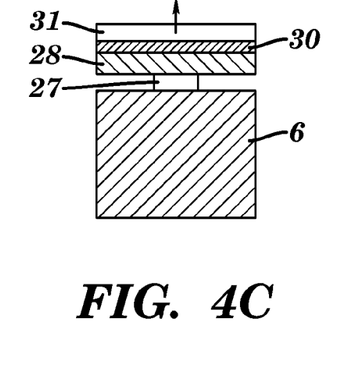
FIG. 4C is a side, cross-sectional view of a portion of yet another microneedle assembly.

The glucose responsive material can be configured in a number of geometries shown in FIGS. 4A-4C. FIG. 4A shows silicon post 6 holding a two layer system supported by spacer 27, comprising a magnetoelastic layer 25 supporting a glucose responsive polymer layer 26. As layer 26 swells, it gains mass and volume, hence modifying the resonant frequency of the mechanically clamped magnetoelastic layer 25. Changes in resonant frequency of layer 25 are measured by monitoring the ac impedance of sensing windings 10 and correlated to glucose concentration. A detachable sensing element may be achieved by reducing the footprint of spacer 27, modifying its interfacial surface energy relative to post 6, or increasing the footprint of layer 25 and spacer 27 relative to the width of post 6.

Examples of magnetoelastic materials that can be used for layer 25 include soft magnetic materials with high permeability commonly used for transformer cores. Any glucose responsive polymer such as polyvinyl alcohol (PVA) blends and composites that change volume or mass as a function of glucose may be used.

FIG. 4B shows another sensing element comprising a mechanically resonant nonmagnetic layer 28 supporting a glucose responsive material with magnetic properties 29, e.g. a ferrogel. An AC magnetic field 24 sampling 29 in turn induces cyclic forces on layer 28, causing it to resonate at one or more characteristic frequencies. A change in mass or volume of the glucose responsive material will modify the overall resonant frequency of layers 28 and 29 that is detected by sensing windings 10.

A three-layer system comprising a nonmagnetic resonant layer 28, a magnetic composite layer 30, and a glucose responsive material is shown in FIG. 4C. Ferrogel magnetoelastic layers may also be used in nonresonant conditions by monitoring changes in impedance of sensing windings 10 as a function of ferrogel swelling. A calibration curve relating resonant frequency versus chemical concentration is needed for devices shown in FIG. 4A-4C.

Figure 5A:
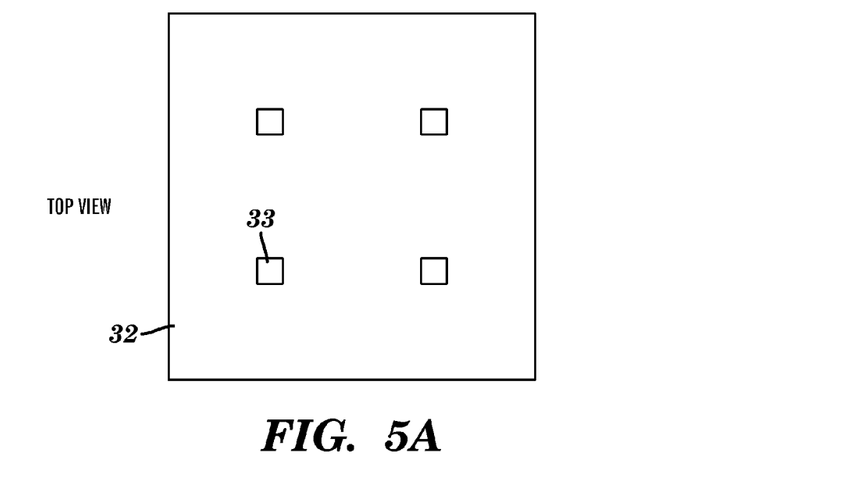
FIG. 5A is a top view of an alternate configuration of a microneedle array.
Figure 5B:
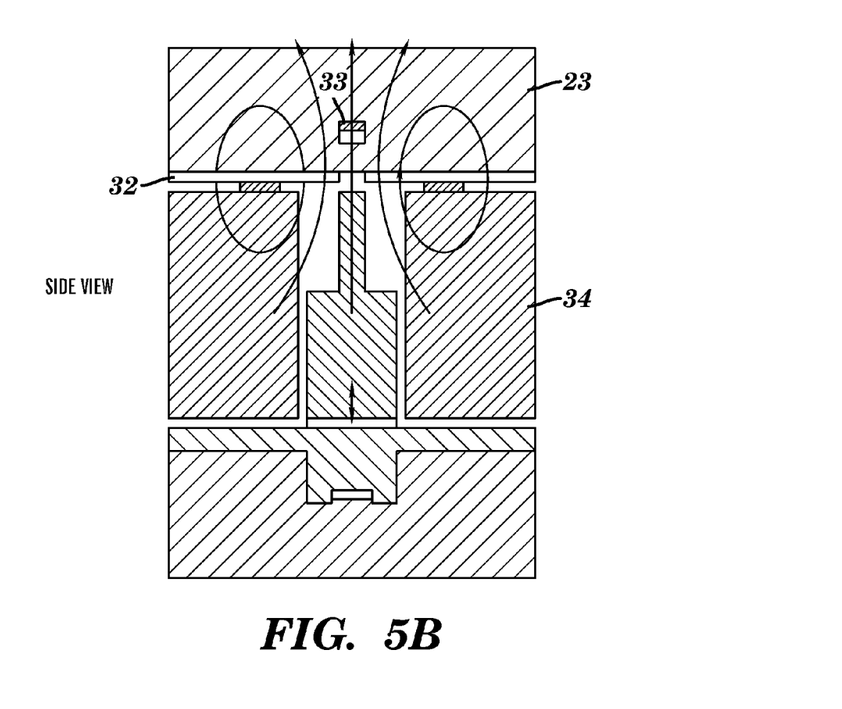
FIG. 5B is a side, cross-sectional view of a microneedle assembly in the microneedle array shown in FIG. 5A.

FIG. 5A-5B shows an alternate configuration for the microneedle array where the chemical sensing element is not fabricated integral to the needle. In this case, a thin support film 32 patterned with sensing elements 33 is aligned with microneedle array 34 such that each sensing element on film 32 sits over an associated addressable microneedle. Upon actuation, microneedles punch a hole through film 32 and drive the sensing elements 33 into subject 23. Sensing elements 33 are left within 23 and continue to be monitored by the respective sensing winding.

Figure 6:
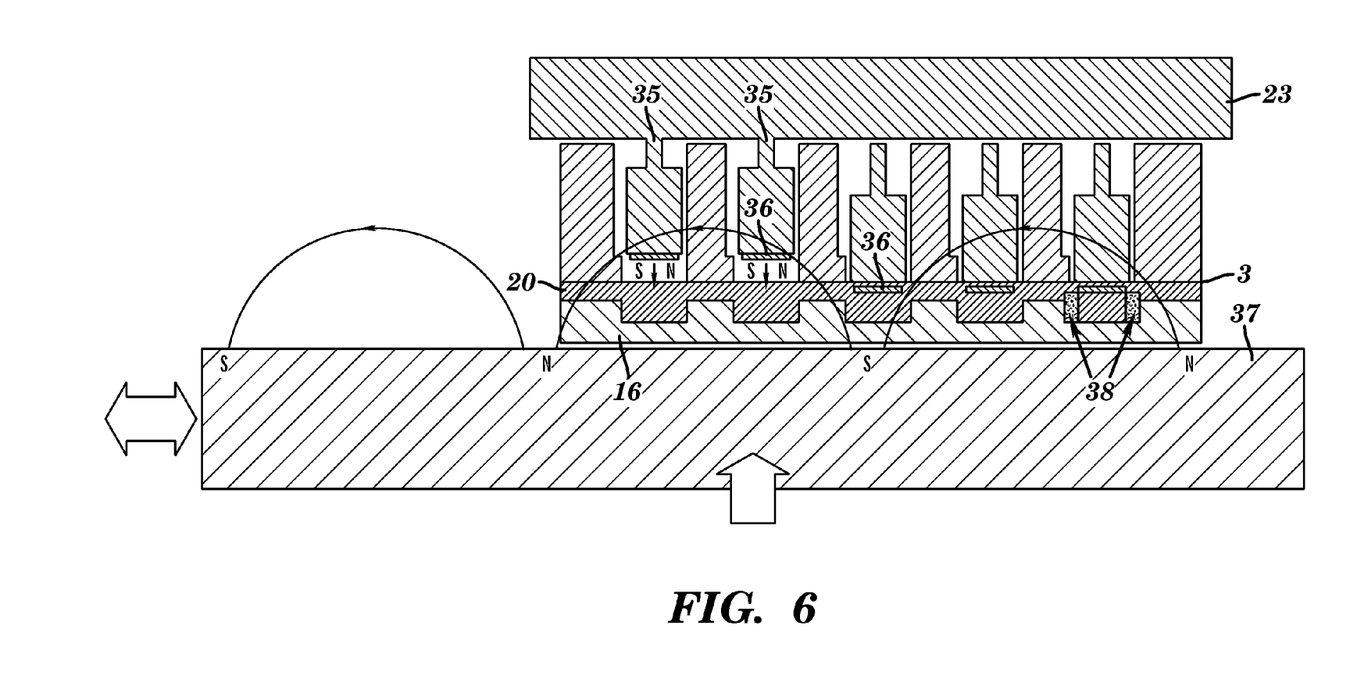
FIG. 6 is a side, cross-sectional view of another microneedle array.

Removal of actuated needles used in configuration 3a may be accomplished as shown in FIG. 6, although other types or removal systems can be used. In this case, a set of actuated needles 35 are removed from subject 23 after have completed their measurement process. To accomplish this, an additional soft magnetic layer or tape is patterned as pads 36 on the bottom surface of microneedle bases 7. When an external magnet 37 is placed in proximity to the microneedle array, each patterned soft magnetic pad 36 magnetizes in a polarity such that it is attracted toward the external magnet. The attractive force pulls the microneedle away from subject 23 as shown in FIG. 6. Although the magnet shown is periodically poled along the array direction, other poling geometries may be used. Magnet 37 may be brought in contact in a direction normal to the array surface or moved tangentially along the surface. The magnetic field will reverse in direction during the process but the force on the microneedles will be attractive toward the magnet. Since magnet 37 will also induce an attractive force on the unactuated needles, layer 3 provides mechanical resistance against this motion. Optional mechanical stops 38 may be fabricated onto or as part of substrate 16 to enhance the mechanical resistance. Stops 38 must allow for liquid filling of liquid channels 20.

Although the present invention has been described in considerable detail with reference to certain preferred versions thereof, other versions are possible. For example, the microneedles can be comprised of glass. Therefore, the spirit and scope of the appended claims should not be limited to the description of the preferred versions contained herein.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features. Additionally, the recited order of processing elements or sequences, or the use of numbers, letters, or other designations therefore, is not intended to limit the claimed processes to any order except as may be specified in the claims.

Any element in a claim that does not explicitly state "means" for performing a specified function or "step" for performing a specified function should not be interpreted as a "means" or "step" clause as specified in 35 U.S.C. §112. Accordingly, the invention is limited only by the following claims and equivalents thereto.

What is claimed is:

1. A blood monitoring system comprising:
   a substrate with one or more wells;
   one or more needles with one of the needles in each of the wells;
   an actuating system that moves the needles at least partially out of the wells when activated;
   one or more sensors, with one of the sensors on each of the needles wherein at least one of the sensors comprises a glucose responsive magnetic material on a mechanically resonant nonmagnetic layer;
   a detection system that reads an output of at least one of the sensors; and
   a control system that controls the activation of the actuating system and the reading of an output from at least one of the sensors by the detection system.

2. The system as set forth in claim 1 wherein at least one of the wells further comprises a vent slot which extends at least partially along a length of the well.

3. The system as set forth in claim 1 wherein each of the needles comprises a base connected to an insertion post.

4. The system as set forth in claim 1 wherein the actuating system comprises:
   another substrate with one or more hollow regions, wherein at least one of the hollow region is positioned substantially below one of the wells; and
   an actuating device in at least one of the hollow regions and coupled to the control system.

5. The system as set forth in claim 4 wherein the actuating device comprises a resistive element.

6. The system as set forth in claim 1 wherein at least one of the sensors is permanently secured to one of the needles.

7. The system as set forth in claim 1 wherein at least one of the sensors is detachably connected to one of the needles.

8. The system as set forth in claim 1 wherein at least one of the sensors comprises a glucose responsive material on a magnetoelastic layer.

9. The system as set forth in claim 1 wherein at least one of the sensors comprises a glucose responsive polymer layer on a magnetic composite layer.

10. The system as set forth in claim 1 wherein the detection system comprises one or more sensing windings with each of the sensing windings positioned about an opening to each of the wells.

11. The system as set forth in claim 1 further comprising a retraction system that retracts the activated needles at least partially back into the wells.

12. The system as set forth in claim 11 wherein the retraction system comprises:
    at least one magnetic layer at a base of each of the needles; and
    at least one magnetic source which can be positioned adjacent to the base of each of the needles to retract the activated needles.

13. The system as set forth in claim 12 wherein the retraction system further comprises one or more stops to prevent the retraction of needles which have not been activated.

14. The system as set forth in claim 1 wherein the actuating system is configured so that each of the one or more needles is actuated independently.

15. A method for making a blood monitoring system, the method comprising:
    forming one or more needles in a substrate with a well around each of the needles;
    providing an actuating system that move the needles at least partially out of the wells when activated;
    providing one or more sensors on each of the needles;
    positioning a detection system to read an output of at least one of the sensors wherein at least one of the sensors comprises a glucose responsive magnetic material on a mechanically resonant nonmagnetic layer; and
    providing a control system that controls the activation of the actuating system and the reading of an output from at least one of the sensors by the detection system.

16. The method as set forth in claim 15 further comprising providing at least one vent slot which extends at least partially along a length of at least one of the wells.

17. The method as set forth in claim 15 wherein the forming one or more needles further comprises etching each of the needles out of the substrate to comprise a base connected to an insertion post.

18. The method as set forth in claim 15 wherein the providing an actuating system comprises:
    forming one or more hollow regions in another substrate;
    providing an actuating device which is coupled to the control system in one or more of the hollow regions; and
    positioning at least one of the hollow regions substantially below one of the wells.

19. The method as set forth in claim 18 wherein the actuating device comprises a resistive element.

20. The method as set forth in claim 15 wherein providing one or more sensors on each of the needles further comprises permanently securing at least one of the sensors to one of the needles.

21. The method as set forth in claim 15 wherein providing one or more sensors on each of the needles further comprises detachably connecting at least one of the sensors to one of the needles.

22. The method as set forth in claim 15 wherein at least one of the sensors comprises a glucose responsive material on a magnetoelastic layer.

23. The method as set forth in claim 15 wherein at least one of the sensors comprises a glucose responsive material on a magnetic composite layer.

24. The method as set forth in claim 15 wherein the positioning a detection system further comprises positioning one or more sensing windings about an opening to one or more of the wells.

25. The method as set forth in claim 16 further comprising providing a retraction system that retracts the activated needles at least partially back into the wells.

26. The method as set forth in claim 25 wherein the providing a retraction system further comprises:
   attaching at least one magnetic layer at a base of each of the needles; and
   providing at least one magnetic source which can be positioned adjacent to the base of each of the needles to retract the activated needles.

27. The method as set forth in claim 26 wherein the providing a retraction system further comprises providing one or more stops to prevent the retraction of needles which have not been activated.

28. The method as set forth in claim 15 wherein the actuating system is configured so that each of the one or more needles is actuated independently.

* * * * *